United States Patent
Yang

(10) Patent No.: US 10,194,977 B2
(45) Date of Patent: Feb. 5, 2019

(54) ELECTROSURGICAL SYSTEM

(71) Applicant: GYRUS MEDICAL LIMITED, St Mellons, Cardiff (GB)

(72) Inventor: Teo Heng Jimmy Yang, Heath Cardiff (GB)

(73) Assignee: GYRUS MEDICAL LIMITED, Cardiff (GB)

(*) Notice: Subject to any disclaimer, the term of this patent is extended or adjusted under 35 U.S.C. 154(b) by 492 days.

(21) Appl. No.: 14/970,960

(22) Filed: Dec. 16, 2015

(65) Prior Publication Data

US 2016/0175032 A1    Jun. 23, 2016

(30) Foreign Application Priority Data

Dec. 19, 2014 (GB) .................................. 1422776.3

(51) Int. Cl.
*A61B 18/12* (2006.01)
*A61B 18/14* (2006.01)
*A61B 18/00* (2006.01)

(52) U.S. Cl.
CPC ...... *A61B 18/1445* (2013.01); *A61B 18/1206* (2013.01); *A61B 2018/0063* (2013.01); *A61B 2018/00607* (2013.01); *A61B 2018/124* (2013.01); *A61B 2018/128* (2013.01)

(58) Field of Classification Search
CPC ............ A61B 18/1206; A61B 18/1445; A61B 2018/00607; A61B 2018/0063; A61B 2018/124; A61B 2018/128
See application file for complete search history.

(56) References Cited

U.S. PATENT DOCUMENTS

| | | | |
|---|---|---|---|
| 6,174,309 B1 | 1/2001 | Wrubleski et al. | |
| 7,204,835 B2 | 4/2007 | Latterell et al. | |
| 7,214,224 B2 | 5/2007 | Goble | |
| 2005/0171533 A1* | 8/2005 | Latterell | A61B 18/1445 606/48 |

FOREIGN PATENT DOCUMENTS

| | | |
|---|---|---|
| WO | 99/66850 | 12/1999 |
| WO | 2008/142404 | 11/2008 |

OTHER PUBLICATIONS

Search Report in UK Application No. GB1422776.3 dated Jun. 5, 2015.

* cited by examiner

*Primary Examiner* — Daniel W Fowler
(74) *Attorney, Agent, or Firm* — Oliff PLC

(57) ABSTRACT

An electrosurgical system includes an electrosurgical generator and an electrosurgical instrument with opposing first and second jaw members movable relative to one another between open and closed positions. The first and second jaw member include, respectively, a cutting electrode and at least a first sealing electrode separated therefrom by an insulating member, and at least a second sealing electrode. The generator includes an energy source for producing at least a cutting RF waveform, first, second and third output connections connected to the cutting electrode, first sealing electrode and second sealing electrode, respectively, and a switching circuit rapidly alternating between a first condition to direct the cutting RF waveform between the first and second output connections and hence the cutting and first sealing electrodes, and a second condition to direct the cutting RF waveform between the first and third output connections, and hence the cutting and second sealing electrodes.

13 Claims, 5 Drawing Sheets

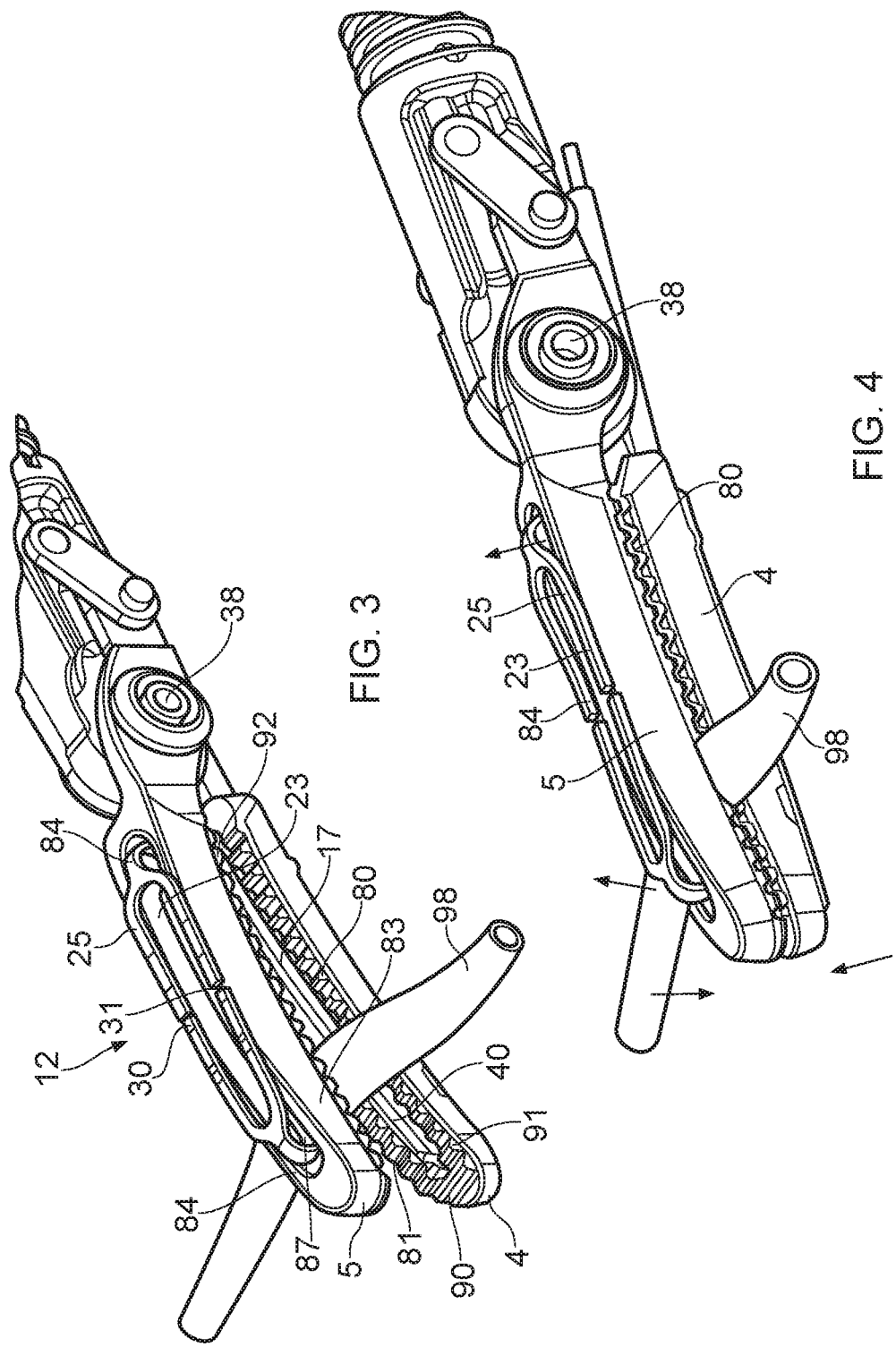

ELECTROSURGICAL SYSTEM

CROSS-REFERENCE TO RELATED APPLICATION

This application claims priority to United Kingdom Application No. 1422776.3, filed 19 Dec. 2014, the entire contents of which are incorporated herein by reference.

TECHNICAL FIELD

Embodiments of the invention relate to an electrosurgical system for cutting tissue, comprising an electrosurgical instrument and an associated electrosurgical generator. Such systems are commonly used for the treatment of tissue in surgical intervention, most commonly in "keyhole" or minimally invasive surgery, but also in "open" surgery.

BACKGROUND TO THE INVENTION AND PRIOR ART

It is known to provide an electrosurgical instrument in which the cutting of tissue is effected by means of an elongate electrosurgical electrode extending along the inner surface of one of a pair of jaw elements. U.S. Pat. Nos. 6,174,309 and 7,204,835 disclose two examples of this kind of instrument. U.S. Pat. No. 7,204,835 discloses an arrangement in which tissue may be cut by the forward movement of a jawed instrument with the jaws held in an open position, a so-called "running cut". Some embodiments of the present invention attempt to provide an improvement to an arrangement instrument such as this.

SUMMARY OF THE INVENTION

Accordingly, from one aspect some embodiments of the invention provide an electrosurgical system including an electrosurgical instrument and an electrosurgical generator, the electrosurgical instrument including:
  a pair of opposing first and second jaw members, at least one of the jaw members being movable relative to the other between a first open position in which the jaw members are disposed in a spaced relation relative to one another, and a second closed position in which the jaw members cooperate to grasp tissue therebetween,
  the first jaw member including a cutting electrode and at least a first sealing electrode separated from the cutting electrode by an insulating member therebetween,
  the second jaw member including at least a second sealing electrode,
  the electrosurgical generator including
  a source of radio frequency energy capable of producing at least a cutting RF waveform,
  first, second and third output connections connected to the cutting electrode, first sealing electrode and second sealing electrode respectively of the electrosurgical instrument,
  the generator further including a switching circuit, and a controller, the controller being such that when a cutting RF waveform is selected, the switching circuit rapidly alternates between a first condition in which it directs the cutting RF waveform between the first and second output connections and hence the cutting electrode and the first sealing electrode, and a second condition in which it directs the cutting RF waveform between the first and third output connections and hence the cutting electrode and the second sealing electrode.

The first and second jaw members preferably each have an inner facing surface between which the tissue is grasped when the jaw members are in their closed position, the cutting electrode being located on the inner facing surface of the first jaw member. The instrument is capable of cutting tissue using at least two different techniques. A first technique is to close the first and second jaw members grasping tissue therebetween, and activate the generator to supply a cutting RF waveform to the cutting electrode. In this arrangement, an RF cutting current flows from the cutting electrode to one or both of the first and second sealing electrodes. A second technique is to hold the first and second jaw members partially open, and move the instrument in a forward direction against tissue entering the V-shaped gap between the first and second jaw members. With a cutting RF waveform supplied to the cutting electrode, the tissue is severed in a "running cut" in a manner similar to moving open scissors forwardly through wrapping paper. Once again, in this arrangement, an RF cutting current flows from the cutting electrode to one or both of the first and second sealing electrodes, cutting the tissue as it comes into contact with the cutting electrode.

To optimise the performance of the instrument when it is used in the first technique requires a different set-up to that needed to optimise the performance of the instrument for use in the second technique. The first technique with tissue grasped between the stationary jaws works best if the current flows from the cutting electrode through the tissue to the sealing electrode on the opposite jaw member. However, when the instrument is used for a running cut, the instrument works best if current flows from the cutting electrode to the sealing electrode on the same jaw as the cutting electrode. Prior art systems use one arrangement, good for one technique but sub-optimum for the other. However, in the present system, the controller and switching circuit rapidly alternates the connections such that current flows from the cutting electrode firstly to the first sealing electrode and then to the second sealing electrode in a rapidly alternating, repeating sequence. Thus, whichever technique is being employed by the user of the instrument, the current flow from the cutting electrode is capable of efficiently cutting tissue.

Preferably, the first sealing electrode comprises a shim having first and second sealing surfaces extending along a length of the jaw and being separated by an insulating member therebetween. Conveniently, the cutting electrode is supported on the insulating member between the first and second sealing surfaces. In this way, the sealing surfaces are provided on each side of the cutting electrode, whether they are used as return electrodes for the cutting electrode, or as tissue coagulating electrodes (as will be described later).

Conveniently, the second sealing electrode also comprises a shim having first and second sealing surfaces extending along a length of the jaw and being separated by a non-conductive area therebetween. Typically, the cutting electrode is disposed opposite the non-conductive area between the first and second sealing surfaces of the second sealing electrode. In this way, when the first and second jaw members are closed, the tissue cutting electrode is still separated from the first and second sealing surfaces on the opposite jaw. Conceivably, the non-conductive area is an insulating member located between the first and second sealing surfaces of the second sealing electrode. Alternatively, the non-conductive area is a gap located between the first and second sealing surfaces of the second sealing electrode.

The source of radio frequency energy is preferably additionally capable of producing at least a coagulating RF waveform. The controller of the electrosurgical generator is preferably such that, when a coagulating RF waveform is selected, the switching circuit directs the coagulating RF waveform between the second and third output connections and hence the first and second sealing electrodes. In this way, the electrosurgical instrument is capable of coagulating tissue grasped between the jaw members, whether prior to tissue cutting or to cauterise bleeding caused by the previous cutting of tissue.

From another aspect embodiments of the invention also provide a method of operating an electrosurgical system including an electrosurgical instrument and an electrosurgical generator, the electrosurgical instrument including a pair of opposing first and second jaw members, at least one of the jaw members being movable relative to the other between a first open position in which the jaw members are disposed in a spaced relation relative to one another, and a second closed position in which the jaw members cooperate to grasp tissue therebetween, the first jaw member including a cutting electrode and at least a first sealing electrode separated from the cutting electrode by an insulating member therebetween, the second jaw member including at least a second sealing electrode, the electrosurgical generator including a source of radio frequency energy capable of producing at least a cutting RF waveform and first, second and third output connections connected to the cutting electrode, first sealing electrode and second sealing electrode respectively of the electrosurgical instrument, the method comprising: i) in a first activation condition supplying, from the generator, a cutting RF waveform between the first and second output connections and hence the cutting electrode and the first sealing electrode; ii) in a second activation condition supplying, from the generator, the cutting RF waveform between the first and third output connections and hence the cutting electrode and the second sealing electrode; and iii) automatically rapidly alternating between the first and second activation conditions. With this operation optimal current flow is obtained automatically, by virtue of the rapid alternation between the first and second activation conditions, to permit both a grasping and cut operation, and a "running cut" operation, as discussed previously.

As a consequence, in one embodiment the method further comprises positioning the jaw members around tissue to be cut, and moving the jaw members into the second closed position to grasp the tissue to be cut therebetween. The automatic alternation between the first and second activation conditions (when the instrument is activated) then causes the grasped tissue to be cut.

In addition, in a further embodiment the method further comprises positioning the jaw members around tissue to be cut, and whilst maintaining the jaw members in an open position moving the jaw members in a forward direction against the tissue so as to cut through the tissue to be cut. Therefore, a "running cut" form of surgical cut through can also be obtained, without having to close the jaws around tissue, or manually select another mode of operation of the generator.

DESCRIPTION OF THE DRAWINGS

Embodiments of the present invention will now be further described, by way of example only, with reference to the accompanying drawings, in which:

FIG. 3 is a perspective view of the distal part of an electrosurgical instrument capable of being used in the system of FIG. 1, shown in an open configuration, FIG. 4 is a perspective view of the distal part of an electrosurgical instrument capable of being used in the system of FIG. 1, shown in a closed configuration.

DESCRIPTION OF THE EMBODIMENTS

Figure 1:
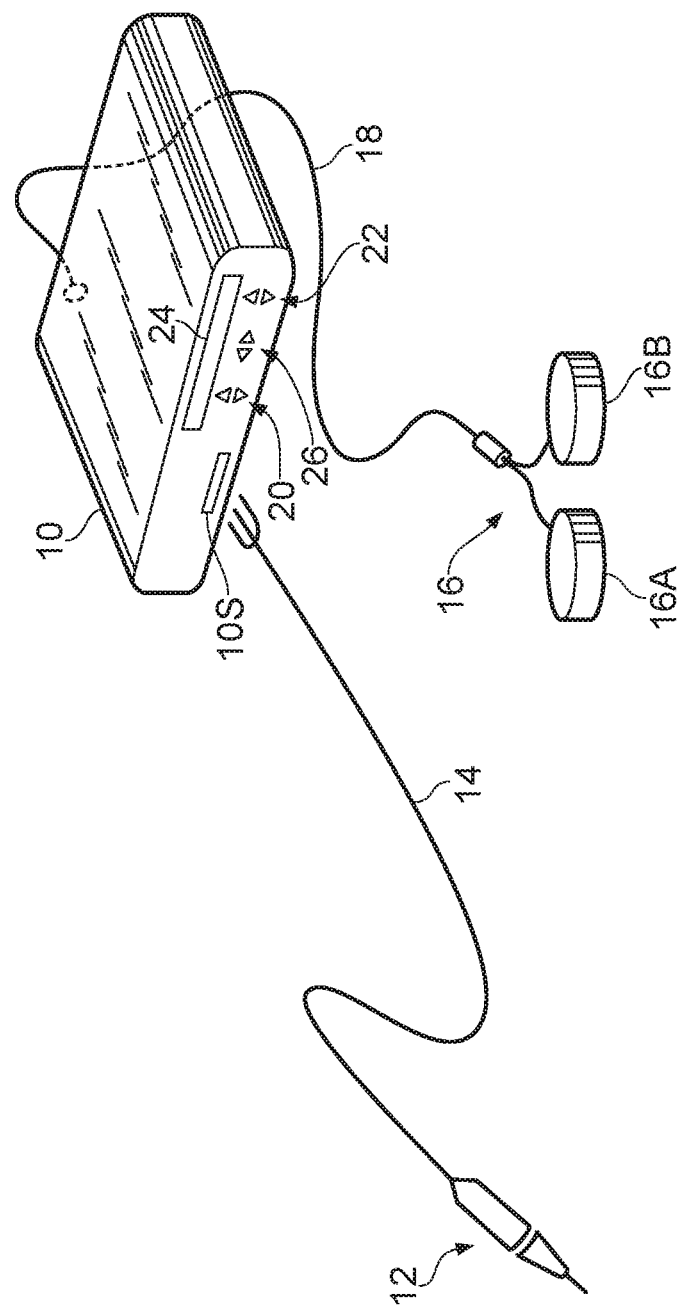
FIG. 1 is a schematic diagram of an embodiment of an electrosurgical system in accordance with the present invention.

Referring to FIG. 1, a generator 10 has an output socket 10S providing a radio frequency (RF) output for an instrument 12 via a connection cord 14. Activation of the generator may be performed from the instrument 12 via a connection in cord 14 or by means of a footswitch unit 16, as shown, connected to the rear of the generator by a footswitch connection cord 18. In the illustrated embodiment footswitch unit 16 has two footswitches 16A and 16B for selecting a coagulation mode and a cutting mode of the generator respectively. The generator front panel has push buttons 20 and 22 for respectively setting coagulation and cutting power levels, which are indicated in a display 24. Push buttons 26 are provided as a means for selection between alternative coagulation and cutting waveforms.

Figure 2:
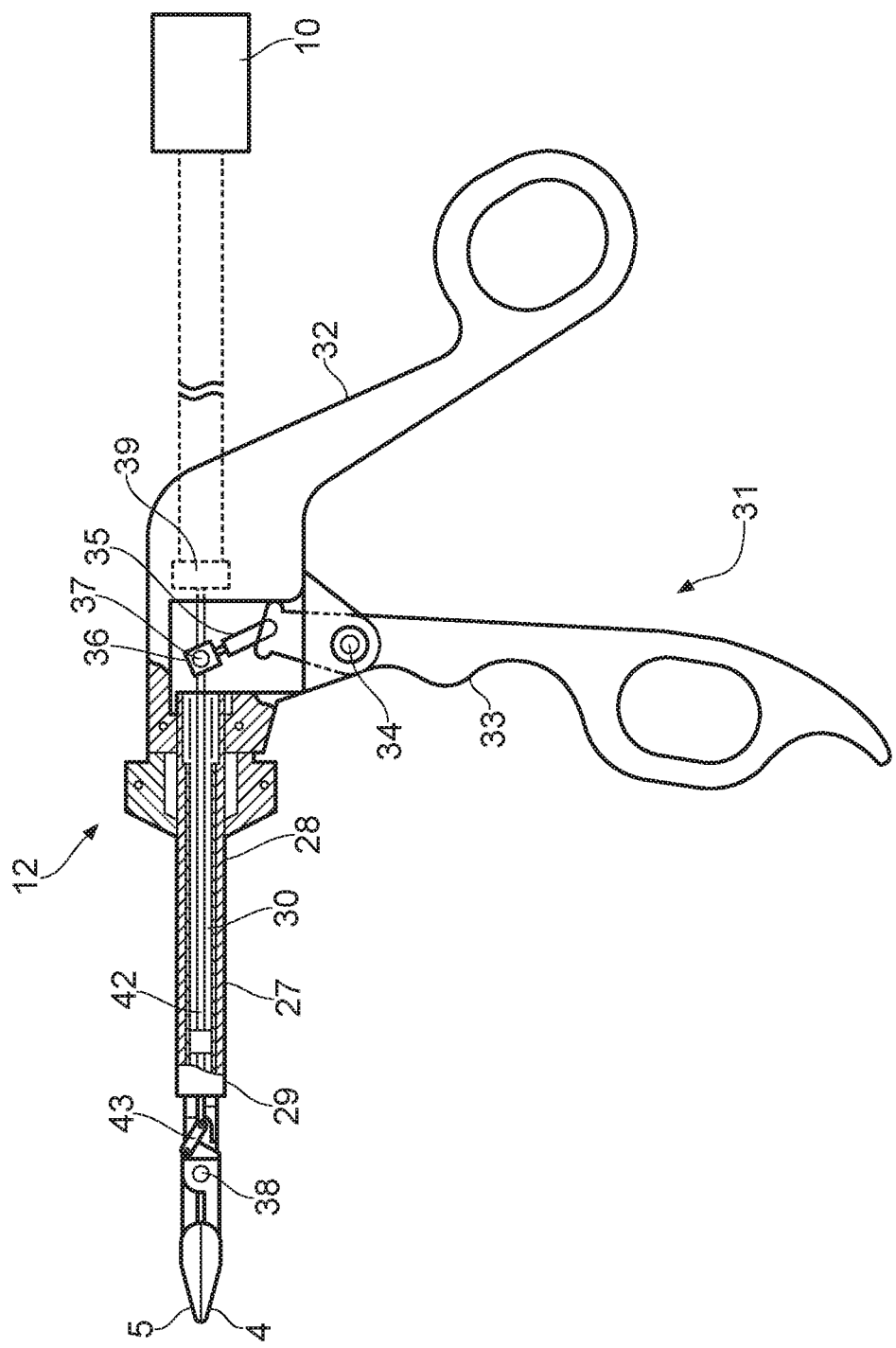
FIG. 2 is a schematic sectional view of an electrosurgical instrument capable of being used in the system of FIG. 1.

FIG. 2 shows the instrument 12 in which the jaw members 4 & 5 are opened and closed by means of a scissors-type handle arrangement. The instrument 12 includes an elongated tubular shaft 27 with a proximal end 28 distal end 29, and a lumen 30 which extends for the entire length of the tubular member. At the proximal end 28 of the tubular member 27 is a scissors-type handle assembly 31 with a first handle 32 and a second handle 33. The second handle 33 is pivotable with respect to the first, about pivot pin 34. In a known design of actuation mechanism, the second handle 33 has a pin 35 affixed to the top thereof, such that movement of the handle causes a corresponding movement to a sphere 37 supported in a U-shaped cradle 36.

Fitted into the distal end 29 of the tubular member 27 is the forceps jaw assembly, comprising the first jaw member 4 and the second jaw member 5, pivotally joined to each other by an insulated rivet 38. As described previously, jaw members 4 & 5 are provided with various electrodes as will be described later, these electrodes being supplied by power from the generator 10 by means of leads (not shown) located within the lumen 30 and terminating in a connector 39, by which the instrument 12 can be attached to the generator 10. A push rod 42 also extends through the lumen 30 and acts on links 43 attached to the jaw members 4 & 5. The proximal end of the push rod 42 passes through the sphere 37. In this way movement of the second handle 33 with respect to the first handle 32 causes a corresponding movement to a sphere 37, the push rod 42, and hence causes the jaw members 4 & 5 to move between their open and closed positions.

The forceps jaw assembly is more particularly shown in FIGS. 3 & 4. The jaw member 4 is provided with a conductive shim 90, having two tissue-contacting surfaces 80 & 81, on either side of a groove 91, in which is located an insulator 17, typically of ceramic or other insulating material. The jaw member 4 is also provided with a relatively-long, but narrow cutting electrode 40 mounted on the insulator 17.

As shown in FIG. 3, the cutting electrode 40 is in the form of an elongate rail, extending along the length of the jaw member 4. The rail 40 is mounted on top of the ceramic insulator 17 such that it is insulated from the shim 90. The rail 40 is typically 100 to 200 microns in width, and protrudes from the ceramic insulator 17 by a distance of approximately 50 microns. When the jaw assembly is in its closed position, the rail 40 is received in a corresponding longitudinal recess 23 in the jaw member 5, as will now be described in further detail.

The recess 23 runs completely through the jaw member 5 from top to bottom, creating an opening therein. The jaw member 5 also has a conductive shim 92, divided by the recess 23 into two tissue-contacting surfaces 82 & 83. Received within the recess 23 is a support member 84 in the form of a sprung frame 25, attached to the top of the jaw member 5 by welding at positions 30 and 31. Depending from the frame 25 is a longitudinally extending anvil 87, formed of an insulating polymer material, and aligned with the cutting electrode 40 in the jaw member 4. When the jaw members 4 and 5 are closed, as shown in FIG. 4, the anvil 87 pushes tissue 98 against the cutting electrode 40.

Figure 5:
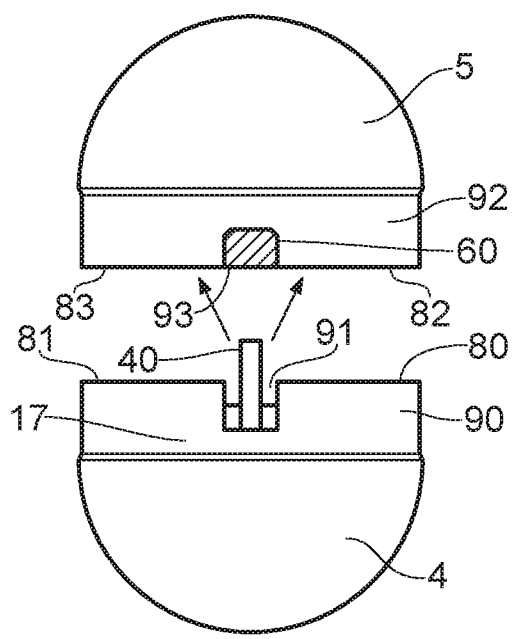
FIGS. 5 to 7 are schematic sectional views of the distal part of an alternative embodiment of electrosurgical instrument used in the system of FIG. 1.

FIG. 5 shows a similar but not identical design of jaw assembly, in which unchanged components are designated with the same reference numerals. As opposed to the recess 23 and support member 84, the jaw member 5 is provided with an insulating spacer 60 in a groove 93 between the tissue-contacting surfaces 82 & 83. The insulating spacer 60 lies opposite the cutting electrode 40. FIG. 5 shows the optimum current flow when tissue (not shown in FIG. 5) is grasped between the jaw members 4 & 5. Current flows from the cutting electrode 40 to the shim 92 located on the jaw 5 rather than to the shim 90 located on the jaw 4.

Figure 6:
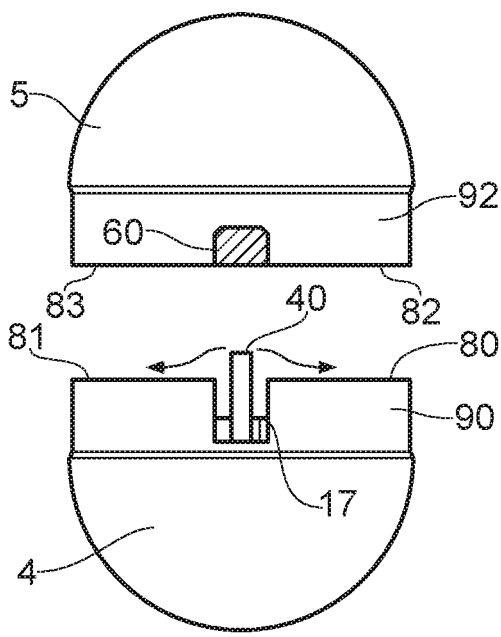

FIG. 6 shows the optimum current flow when the jaws are being used to perform a running cut. Current flows from the cutting electrode 40 to the shim 90 located on the jaw 4 rather than to the shim 92 located on the jaw 5. In this way, even if tissue (not shown) is not in contact with the jaw 5, current will still pass through the tissue between the electrodes present on the jaw 4.

Figure 7:
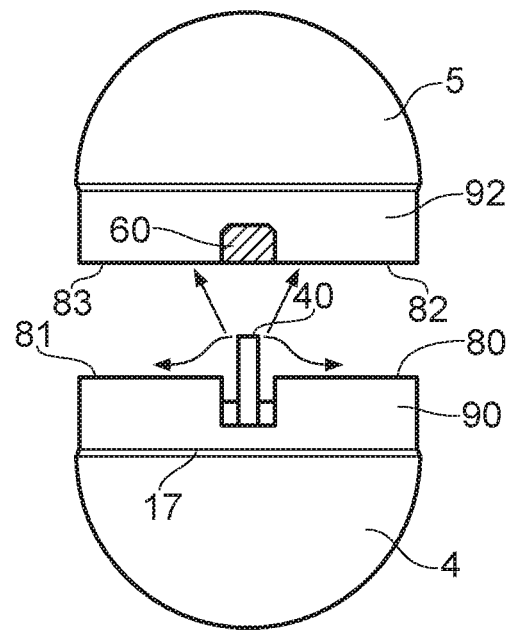

FIG. 7 shows the current flow in the system of the present invention. For part of a predetermined duty cycle, current will flow between the cutting electrode 40 and the shim 92 located on the jaw 5. For the remainder of the predetermined duty cycle, current will flow between the cutting electrode 40 and the shim 90 located on the jaw 4. Therefore, regardless of whether the instrument 12 is being used in a running cut or to cut tissue grasped between the jaw members, the current flow will be appropriate to that requirement for that part of the duty cycle associated with either FIG. 5 or FIG. 6. Therefore, the instrument will produce effective tissue cutting, regardless of whichever technique is employed by the user of the instrument.

Figure 8:
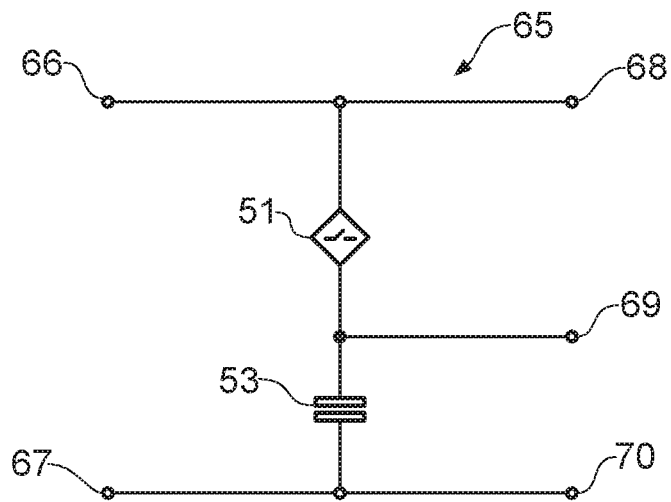
FIG. 8 is a schematic diagram of a switching circuit used in the system of FIG. 1, and FIGS. 9A and 9B are circuit diagrams of two electronic switching devices for the switching circuit of FIG. 8.

FIG. 8 shows a switching circuit capable of producing the rapidly alternating arrangement of FIG. 7. The switching circuit is shown generally at 65 and comprises input connections 66 and 67 connected respectively to the two output lines of the generator 10. Switching circuit 65 has three output connections 68, 69 and 70. Output connection 68 is connected to the shim 90 in the device of FIGS. 5 to 7. Output connection 69 is connected to the shim 92, while output connection 70 is connected to the cutting electrode 40 in the device of FIGS. 5 to 7. An electronic switch device 51 is connected between output connections 68 and 69. The switch 51 is capable of rapidly making and breaking the connection between the output lines 68 and 69. A capacitor 53 is connected between the output connections 69 and 70, the capacitor typically having a value of between 1 and 10 nF.

When the user actuates the footswitches 16A or 16B to operate the instrument 12 a cutting mode, the generator supplies an RF cutting waveform to the input connections 66 and 67. The switch device 51 operates such that for part of duty cycle, the switch device is open such that there is open circuit between the output connections 68 and 69. During this part of the cycle, the cutting RF waveform is supplied between cutting electrode 40 and the shim 90, via output connections 70 and 68, respectively. Conversely, for the opposite part of the duty cycle, the switching device 51 is closed such that output connections 68 and 69 are in electrical communication one with the other. Thus, during this part of the duty cycle, the signal is supplied between the cutting electrode 40 and shim 92, via output connections 70 and 69, respectively, with the capacitor 53 providing a potential difference therebetween.

Figure 9A:
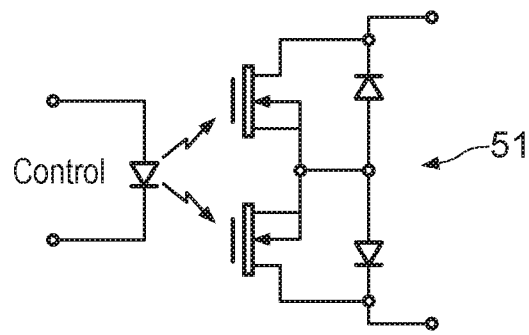
Figure 9B:
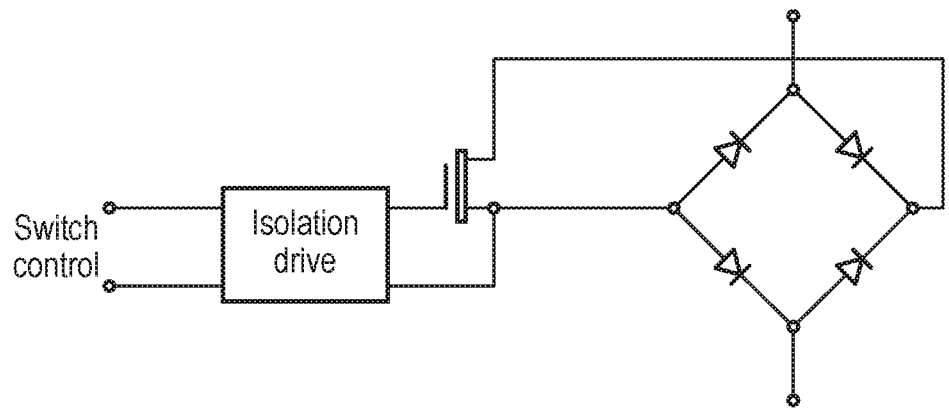

Switching device 51 may comprise an AC opto-relay such as the optically coupled dual FET arrangement shown in FIG. 9A. Another switching device providing isolation between control circuitry and the output lines is the combination of an AC bridge and a single MOSFET switch controlled via an isolating driver, a shown in FIG. 9B.

When the user wishes to coagulate tissue grasped between the jaws 4 & 5, the generator supplies an RF coagulating waveform to the input connections 66 and 67, and the switch circuit operates to supply the waveform between the first and second pairs of tissue sealing plates, via output connections 68 & 69. Conceivably, the switching circuit can operate in a blended cut and coagulation mode. In this blended mode, the RF coagulating waveform is supplied to output connections 68 & 69 for part of the duty cycle, and the RF cutting waveform is supplied between output connections 68 and 70 and output connections 69 and 70 in an alternating manner for the remainder of the duty cycle.

The invention claimed is:

1. An electrosurgical system including an electrosurgical instrument and an electrosurgical generator,
   the electrosurgical instrument including:
      a pair of opposing first and second jaw members, at least one of the jaw members being movable relative to the other between a first open position in which the jaw members are disposed in a spaced relation relative to one another, and a second closed position in which the jaw members cooperate to grasp tissue therebetween, the first jaw member including a cutting electrode and at least a first sealing electrode separated from the cutting electrode by an insulating member therebetween, the second jaw member including at least a second sealing electrode,
   the electrosurgical generator including:
      a source of radio frequency energy capable of producing at least a cutting RF waveform, first, second and third output connections connected to the cutting electrode, first sealing electrode and second sealing electrode respectively of the electrosurgical instrument, the generator further including a switching circuit, and
      a controller, the controller being such that when a cutting RF waveform is selected, wherein:

the switching circuit rapidly alternates between a first condition in which it directs the cutting RF waveform only between the first and second output connections and hence the cutting electrode and the first sealing electrode, and a second condition in which it directs the cutting RF waveform only between the first and third output connections and hence the cutting electrode and the second sealing electrode.

2. The electrosurgical system according to claim 1, wherein the first and second jaw members each have an inner facing surface between which the tissue is grasped when the jaw members are in their closed position, the cutting electrode being located on the inner facing surface of the first jaw member.

3. The electrosurgical system according to claim 2, wherein the first sealing electrode comprises a shim having first and second sealing surfaces extending along a length of the jaw and being separated by an insulating member therebetween.

4. The electrosurgical system according to claim 3, wherein the cutting electrode is supported on the insulating member between the first and second sealing surfaces.

5. The electrosurgical system according to claim 4, wherein the second sealing electrode comprises a shim having first and second sealing surfaces extending along a length of the jaw and being separated by a non-conductive area therebetween.

6. The electrosurgical system according to claim 5, wherein the cutting electrode is disposed opposite the non-conductive area between the first and second sealing surfaces of the second sealing electrode.

7. The electrosurgical system according to claim 5, wherein the non-conductive area is an insulating member located between the first and second sealing surfaces of the second sealing electrode.

8. The electrosurgical system according to claim 5, wherein the non-conductive area is a gap located between the first and second sealing surfaces of the second sealing electrode.

9. The electrosurgical system according to claim 1, wherein the source of radio frequency energy is additionally capable of producing at least a coagulating RF waveform.

10. The electrosurgical system according to claim 9, wherein the controller of the electrosurgical generator is such that, when a coagulating RF waveform is selected, the switching circuit directs the coagulating RF waveform between the second and third output connections and hence the first and second sealing electrodes.

11. A method of operating an electrosurgical system including an electrosurgical instrument and an electrosurgical generator, the electrosurgical instrument including a pair of opposing first and second jaw members, at least one of the jaw members being movable relative to the other between a first open position in which the jaw members are disposed in a spaced relation relative to one another, and a second closed position in which the jaw members cooperate to grasp tissue therebetween, the first jaw member including a cutting electrode and at least a first sealing electrode separated from the cutting electrode by an insulating member therebetween, the second jaw member including at least a second sealing electrode, the electrosurgical generator including a source of radio frequency energy capable of producing at least a cutting RF waveform and first, second and third output connections connected to the cutting electrode, first sealing electrode and second sealing electrode respectively of the electrosurgical instrument, the method comprising:
   i) in a first activation condition supplying, from the generator, a cutting RF waveform only between the first and second output connections and hence the cutting electrode and the first sealing electrode;
   ii) in a second activation condition supplying, from the generator, the cutting RF waveform only between the first and third output connections and hence the cutting electrode and the second sealing electrode; and
   iii) automatically rapidly alternating between the first and second activation conditions.

12. The method according to claim 11, and further comprising positioning the jaw members around tissue to be cut, and moving the jaw members into the second closed position to grasp the tissue to be cut therebetween.

13. The method according to claim 11, and further comprising, positioning the jaw members around tissue to be cut, whilst maintaining the jaw members in an open position, moving the jaw members in a forward direction against the tissue so as to cut through the tissue to be cut.

* * * * *